United States Patent
Yersin et al.

(10) Patent No.: US 8,815,413 B2
(45) Date of Patent: Aug. 26, 2014

(54) OXAZOLE TRIPLET EMITTERS FOR OLED APPLICATIONS

(75) Inventors: Hartmut Yersin, Sinzing (DE); Oliver Reiser, Regensburg (DE); Qun-li Luo, Chongqing (CN); Stefan Eibauer, Berlin (DE)

(73) Assignee: Merck Patent GmbH, Darmstadt (DE)

( * ) Notice: Subject to any disclaimer, the term of this patent is extended or adjusted under 35 U.S.C. 154(b) by 1033 days.

(21) Appl. No.: 12/375,220

(22) PCT Filed: Jul. 27, 2007

(86) PCT No.: PCT/EP2007/006683
§ 371 (c)(1),
(2), (4) Date: Oct. 30, 2009

(87) PCT Pub. No.: WO2008/012103
PCT Pub. Date: Jan. 31, 2008

(65) Prior Publication Data
US 2011/0062858 A1    Mar. 17, 2011

(30) Foreign Application Priority Data
Jul. 28, 2006 (DE) .................. 10 2006 035 018

(51) Int. Cl.
*H01L 51/54* (2006.01)
*C09K 11/06* (2006.01)

(52) U.S. Cl.
USPC ........... 428/690; 428/917; 313/504; 313/506; 252/301.16; 257/40; 257/102; 257/E51.044; 548/101; 548/228; 548/235

(58) Field of Classification Search
None
See application file for complete search history.

(56) References Cited

U.S. PATENT DOCUMENTS

| | | | |
|---|---|---|---|
| 5,792,568 A | 8/1998 | Emoto et al. | |
| 6,908,783 B1 | 6/2005 | Kuehl et al. | |
| 6,984,591 B1 | 1/2006 | Buchanan et al. | |
| 2002/0042174 A1 | 4/2002 | Kunugi et al. | |
| 2002/0179885 A1 | 12/2002 | Che et al. | |
| 2003/0186080 A1 | 10/2003 | Kamatani et al. | |
| 2003/0205707 A1 | 11/2003 | Chi-Ming et al. | |
| 2004/0065544 A1 | 4/2004 | Igarashi et al. | |
| 2004/0121184 A1 | 6/2004 | Thompson et al. | |
| 2004/0241492 A1 | 12/2004 | Tokuda | |
| 2004/0262576 A1 | 12/2004 | Thompson et al. | |
| 2005/0025994 A1* | 2/2005 | Hanna et al. ............. | 428/690 |
| 2005/0221115 A1 | 10/2005 | Tsuboyama et al. | |
| 2005/0260449 A1 | 11/2005 | Walters et al. | |
| 2006/0071206 A1 | 4/2006 | Stossel et al. | |
| 2006/0115675 A1* | 6/2006 | Haga et al. ............. | 428/690 |
| 2006/0208252 A1 | 9/2006 | Wessels et al. | |
| 2006/0258043 A1 | 11/2006 | Bold et al. | |
| 2007/0111025 A1 | 5/2007 | Lennartz et al. | |
| 2007/0135635 A1 | 6/2007 | Stoessel et al. | |
| 2007/0264524 A1 | 11/2007 | Gessner et al. | |
| 2008/0121870 A1 | 5/2008 | Seth et al. | |
| 2009/0318698 A1 | 12/2009 | Hortmann et al. | |

FOREIGN PATENT DOCUMENTS

| | | |
|---|---|---|
| DE | 4112793 | 10/1992 |
| GB | 1436230 | 5/1976 |
| JP | 03208689 | 9/1991 |
| WO | WO 2004/017043 | 2/2004 |
| WO | WO 2005/086251 | 9/2005 |

OTHER PUBLICATIONS

Gayathri et al. "Cyclometallation of bis-benzimidazole derivatives with rhodium(III) halides." Polyhedron, 1999. vol. 18, pp. 2351-2360.*
Okamoto et al. "Preparation and characterization of luminescent SCS and NCN pincer platinum complexes derived from 3,5-bis(anilinothiocarbonyl)toluene" Organometallics, 2006. vol. 25, pp. 4026-4029.*
Luo et al. "Novel bis(oxazole) pincer ligands for catalysis: Application in Suzuki-Miyaura cross coupling reactions under aerobic conditions." Journal of Molecular Catalysis A: Chemical. 2007, vol. 268, pp. 65-69.*
Adachi, C. et al. "High-efficiency red electrophosphorescence devices," Appl. Phys. Lett. 2001, 78, 1622.

(Continued)

*Primary Examiner* — Michael H Wilson
(74) *Attorney, Agent, or Firm* — Drinker Biddle & Reath LLP

(57) ABSTRACT

The present invention relates to compounds which can be used in particular as ligands, to complexes of formula (I) and (II)

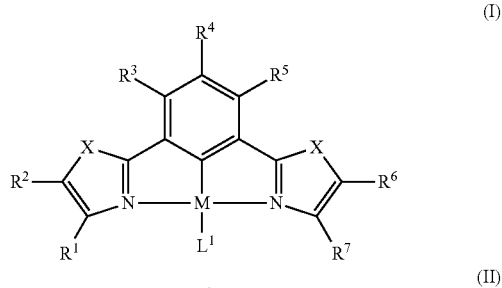

(I)

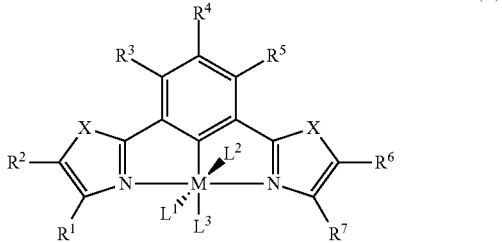

(II)

and also to light-emitting devices and in particular to organic light-emitting devices (OLEDs). In particular, the invention relates to the use of luminescent oxazole-chelate metal complexes as emitters in such devices.

23 Claims, 10 Drawing Sheets

(56) References Cited

OTHER PUBLICATIONS

Beckert, R. et al., "Syntheses and properties of cycloamidines based on 4H-imidazoles," Z. Naturforschung B, vol. 61, No. 4 (2006).
Blochwitz, J., et al., "Low voltage organic light emitting diodes featuring doped phthalocyanine as hole transport material," Applied Physics Letters, vol. 73, No. 6, Aug. 10, 1998, pp. 729-731.
Chassot, L. and Von Zelewsky, A., "Cyclometalated Complexes of Platinum(II): Homoleptic Compounds with Aromatic C, N Ligands," Inorg. Chem. (1987), 26, 2814-2818.
Cocchi, M. et al., "Highly efficient organic electroluminescent devices based on cyclometallated platinum complexes as new phosphorent emitters," Synthetic Metals, 147, 253-256, (2004).
Cocchi, M. et al., "Highly efficient organic electroluminescent light-emitting diodes with a reduced quantum efficiency roll off at large current densities," Applied Physics Letters, 84, 7, 1052-1054 (2004).
Davison, A. et al., "Further Examples of Complexes Related by Electron-Transfer Reactions: Complexes Derived from Bis9trifluoromethyl)-1,2-dithietene," Inorg. Chem. (1964) 3/6 p. 814.
Denmark, S. et al., "Cyclopropanation with Diazomethane and Bis(Oxazoline) Palladium (II) Complexes," Journal of Organic Chemistry, 62, No. 10, May 16, 1997.
Doucet, et al., "Palladium-Based Catalytic Systems for the Synthesis of Conjugated Enynes by Sonogashira Reactions and Related Alkynylations," Angew. Chem. Int. Ed. (2007) 46, 834.
Gareau, Y. et al. "Free Radical Reaction of Diisopropyl Xanthogen Disulfide with Unsaturated Systems," Heterocycles (1998) 48, p. 2003.
Gebauer, T. et al., "Mesoionic bora-tetraazapentalenes—fully reversible two step redox systems," Chemical Communications (2004), (16), 1860-1861.
Huang et al., "Synthesis of Perfluoro-2-alkynenitriles," Tetrahedron Letters (1981) 22, p. 5283.
Krebs et al., "Strained Cyclic Acetylenes, VII Addition of Sulfur and Pyridine-N-Oxide to Seven Membered Cycloalkynes," Heterocycles (1979) 12, p. 1153.
Krespan, C.G.; "Bis-(polyfluoroalkyl)-acetylenes. IV. Fluorinated Dithietenes and Related Heterocyclic Compounds From Bis-(polyfluoroalkyl)-acetylenes and Sulfur," J.Am. Chem. Soc. (1961) 83, 3434.
Lo, K. M., et al., "Synthesis and spectroscopic studies of thienyl triorganotin (IV) compounds," J. Organometal. Chem. (1992), 430, 149.
Marder et al., "Synthesis, Optical Properties, Crystal Stuctures and Phase Behavior of Selectively Fluorinated 1,4-bis(4'-pyridylethynyl)benzenes, 4-(phenylethynyl)pyridines and 9,10-bis(4'-pyridylethynyl)-anthracene, and a $Zn(NO_3)_2$ Coordination Polymer," J. Mater. Chem. (2004) 14, 2395.
Mayer, R., et al. "Synthese der 1,3-Dithiol-2-thione," Angew. Chem. (1964) 76, p. 143.
Nakayama, J. et al., "A Convenient Synthesis of 1,2-Dithietes and 1,2-Dithioxo Compounds Stabilized by Buttressing and Resonance Effects, Respectively, by Sulfuration of Alkynes with Elemental Sulfur," Bull. Chem. Soc. Jpn. (1993) 66, p. 623.

Okada, S. et al. "Substituent effects of iridium complexes for highly efficient red OLEDs," Dalton Trans., 2005, 1583.
Pereira, R. P. et al., "Electrosynthesis and characterization of polypyrrole doped with [Bi(dmit)2]<–>," Synthetic Metals, Apr. 20, 2005, p. 21-26.
Pfeiffer, M. et al., "Controlled doping of phthalocyanine layers by cosublimation with acceptor molecules: A systematic Seebeck and conductivity study," Applied Physics Letters, vol. 73, No. 22 Nov. 20, 1998, pp. 3202-3204.
Schrauzer, A. "Preparation, Reactions, and Structure of Bisdithio-α-diketone Complexes of Nickel, Palladium, and Platinum," J. Am. Chem. Soc. (1965) 87/7 1483-9.
Schrauzer, et al., "Reaktionen von Ubergangsmetallsulfiden mit Alkinen. Zur Kenntnis von Metallkomplexen der α-β-Dithiodiketone," Z. Naturforschg. (1964) 19b, 192-8.
Shinar, J. "Organic Light-Emitting Devices—A Survey," AIP-Press, Springer, New York 2004.
Sonogahsira, et al., "A Convenient Synthesis of Acetylenes: Catalytic Substitutions of Acetylenic Hydrogen with Bromoalkenes, Iodoarenes, and Bromopyridines." Tetrahedron Letters (1975) 50, 4467.
Sotoyama, W. et al. "Efficient organic light-emitting diodes with phosphorescent platinum complexes containing N—C—N-coordinating tridentate ligand," Appl. Phys. Lett. 2005, 86, 153505.
Taguchi, et al., "Comparison of p-type and n-type organic field-effect transistors using nickel coordination compounds," Chemical Physics Letters, Apr. 15, 2006, p. 395-398.
Tang, C.W. et al., "Organic electroluminescent diodes," Applied Physics Letters, vol. 51, No. 12, Sep. 21, 1987, pp. 913-915.
Tarraga, A. et al., "Synthesis and electrochemical study of novel and oxazolo-ferrocene derivatives displaying redox-switchable character," Tetrahedron, 57, 31, Jul. 30, 2001, pp. 6765-6774.
Tung, Y. L. et al. "Organic light-emitting diodes based on charge-neutral Os(II) emitters: generation of saturated red emission with very high external quantum efficiency," J. Mater. Chem., 2005, 15, 460-464.
Yang, X. H. et al. "Polymer electrophosphorescence devices with high power conversion efficiencies," Appl. Phys. Lett. 2004, 84, 2476.
Yersin, H. and Donges, D. "Low-Lying Electronic States and Photophysical Properties of Organometallic Pd(II) and Pt(II) Compounds. Modern Research Trends Presented in Detailed Case Studies," Topics in Curr. Chem. (2001), 214, 81.
Yersin, H. "Highly Efficient OLEDs with Phosphorescent Materials," Wiley-VCH 2006.
International Search Report, International App. No. PCT/EP2007/006683, Nov. 13, 2007.
International Search Report, International App. No. PCT/EP2007/004638, Jul. 23, 2007.
International Search Report, International App. No. PCT/DE2006/002330, Apr. 24, 2007.
International Search Report, International App. No. PCT/DE2007/000587, Sep. 11, 2007.
Disclosure Under 37 C.F.R. 1.56 for U.S. Appl. No. 12/375,220.

\* cited by examiner

Figure 1

| Cathode: Al | 200 nm |
|---|---|
| Intermediate layer: LiF | 0.8 nm |
| Electron transport layer ETL: Alq$_3$ | 40 nm |
| Emitter layer EML: CBP with 6% complex doping | 70 nm |
| Hole transport layer HTL: α-NPD | 30 nm |
| Hole injection layer HIL: CuPc | 10 nm |
| Anode ITO | 40 nm |
| Substrate material, glass | |

ETL = Electron transport layer

EML = Emitter layer

HTL = Hole transport layer

HIL = Hole injection layer

Alq$_3$ = Aluminum-8-hydroxy-quinoline

α-NPD = 4,4'-Bis[N-(1-naphthyl)-N-phenylamino]biphenyl

CuPC = Copper phthalocyanine

CBP = 4,4'-Bis(N-carbozolyl)biphenyl

ITO = Indium tin oxide

Figure 2

| 9 | Cathode |
| 8 | Intermediate layer |
| 7 | ETL |
| 6 | Hole blocking layer |
| 5 | Emitter layer |
| 4 | Electron blocking layer |
| 3 | HTL |
| 2 | Anode, ITO |
| 1 | Substrate material, glass |

Figure 3

| 7 | Cathode, Al: 60 nm |
|---|---|
| 6 | Intermediate layer CsF: 0.8 nm |
| 5 | ETL, Alq$_3$: 40 nm |
| 4 | Emitter layer 10 to 80 nm |
| 3 | HTL, PEDOT:PSS: 50 nm |
| 2 | Anode, ITO: 40 nm |
| 1 | Substrate material, glass |

OXAZOLE TRIPLET EMITTERS FOR OLED APPLICATIONS

The present invention relates to compounds which can be used in particular as ligands, to complexes and also to light-emitting devices and in particular to organic light-emitting devices (OLEDs). In particular, the invention relates to the use of luminescent oxazole-chelate metal complexes as emitters in such devices.

OLEDs (Organic Light Emitting Devices or Organic Light Emitting Diodes) represent a new technology which will dramatically change the display and lighting field. OLEDs consist predominantly of organic layers which can also be manufactured in a flexible and inexpensive manner. MED components can be designed with a large surface area as lighting elements, but also small as pixels for displays.

An overview of the function of OLEDs can be found for example in H. Yersin, Top. Curr. Chem. 2004, 241, 1 and in H. Yersin, "Highly Efficient OLEDs with Phosphorescent Materials", Wiley-VCH 2006.

The function of OLEDs has also been described in C. Adachi et al., Appl. Phys. Lett. 2001, 78, 1622; X. H. Yang et al., Appl. Phys. Lett. 2004, 84, 2476; J. Shinar, "Organic Light-Emitting Devices—A Survey", AIP-Press, Springer, New York 2004; W. Sotoyama et al., Appl. Phys. Lett. 2005, 86, 153505; S. Okada et al., Dalton Trans., 2005, 1583 and Y.-L. Tung et al., J. Mater. Chem., 2005, 15, 460-464.

Since the first reports concerning OLEDs (see e.g. Tang et al., Appl. Phys. Lett. 51 (1987) 913), these devices have been further developed in particular with regard to the emitter materials used; most recently, so-called triplet emitters or phosphorescent emitters have been of interest in particular.

Compared to conventional technologies, such as for example liquid crystal displays (LCDs), plasma displays or cathode ray tubes (CRTs), OLEDs have numerous advantages such as, for example, a low operating voltage, a flat design, highly efficient self-illuminating pixels, a high contrast and a good resolution and also the possibility of displaying all colors. Furthermore, an OLED emits light when an electric voltage is applied, instead of just modulating it. While the OLED has already been the subject of numerous applications and new fields of application have also been opened up, there is still a need for improved OLEDs and in particular for improved triplet emitter materials. In the solutions to date, problems occur in particular with regard to the long-term stability, the thermal stability and also the chemical stability with respect to water and oxygen. Furthermore, many emitters exhibit only a low ability to sublimate. Moreover, important emission colors are often not available with previously known emitter materials. High efficiencies at high current densities or high light densities often also cannot be achieved. Finally, in many emitter materials, problems exist with regard to the reproducibility in manufacturing terms.

It has also been found that the light yield for OLEDs containing metal-organic substances, so-called triplet emitters, can be much greater than for purely organic materials. Due to this property, considerable importance has been placed on the further development of metal-organic materials. Triplet emitters are described for example in WO 2004/017043 A2 (Thompson). WO 2004/016711 A1 (Thompson), WO 03/095587 (Tsuboyama), US 2003/0205707 (Chi-Ming Che), US 2002/0179885 (Chi-Ming Che), US 2003/186080 A1 (J. Kamatani), DE 103 50 606 A1 (Stößel), DE 103 38 550 (Bold), DE 103 58 665 A1 (Lennartz).

One object of the present invention was to provide novel emitter materials, in particular for OLEDs, and also novel light-emitting devices which at least partially overcome the disadvantages of the prior art and which in particular are very stable and can easily be sublimated.

This object is achieved according to the invention by complexes of formula (I) or (II)

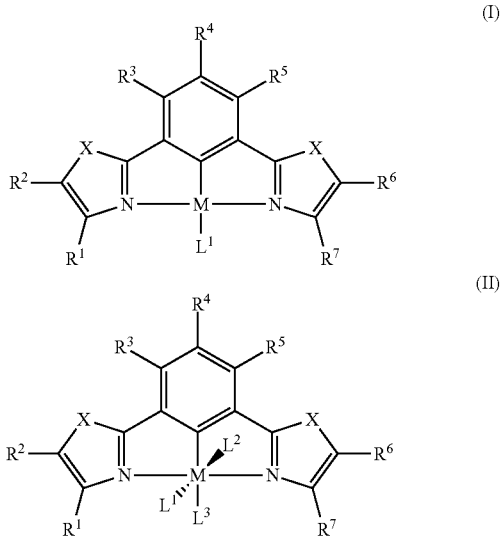

in which M is selected from an element from group 6 to 11 of the 2nd or 3rd period of the transition metals, in particular from Mo, Ru, Rh, Pd, Ag, W, Re, Os, Ir, Pt and Au, X is an element from group 15 or 16 of the Periodic Table and in particular is oxygen,
$R^1$ to $R^7$ independently of one another are each hydrogen, halogen, R', O—R' or N—R'R", in which R' is a hydrocarbon group which may optionally contain heteroatoms and R" is H or has a meaning as defined for R', it also being possible, for two or more groups $R^1$ to $R^7$ to form fused ring systems, and $L^1$, $L^2$ and $L^3$ independently of one another are each a negatively charged or neutral ligand, it being possible for two or more of the ligands and $L^3$ to be bound to one another.

The complexes according to the invention are in particular luminescent compounds. The complexes have a central atom which is selected from an element from group 6-11 of the 2nd and 3rd period of the transition metals, in particular from Mo, Tc, Ru, Rh, Pd, Ag, W, Re, Os, Ir, Pt or Au, preferably from Mo, Ru, Rh, Pd, Ag, W, Re, Os, Ir, Pt or Au, even more preferably from Pt, Pd, Ru, Os or Ir, preferably from Pt or Pd. The central atom is preferably in oxidation stages 0 to +4. With particular preference, the central atom is Pt(II), Ir(III) or Pd(II). According to the invention, the central atom is four-coordinated or six-coordinated. The complexes according to the invention are preferably complexes with a single metal central atom.

The complexes according to the invention furthermore contain a ligand of formula (III):

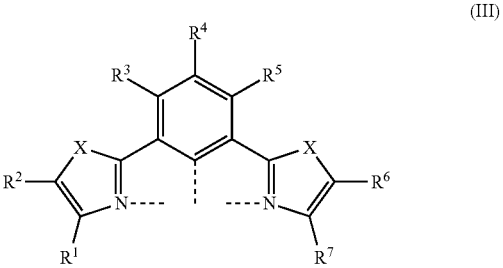

which is also referred to herein as the oxazole ligand. The oxazole ligand is a tridentate ligand. Here, the group X is an element from group 15 (i.e. N, P, As, Sb or Bi), in particular nitrogen, or from group 16 (i.e. O, S, Se, Te or Po), in particular oxygen or sulphur, of the Periodic Table of the Elements. Most preferably, X is oxygen. For the case where X is an element from group 15, the free valency is suitably bound, e.g. to H, alkyl, aryl, etc.

The oxazole ligand furthermore contains radicals R1 to R7 which independently of one another are each hydrogen, halogen or a hydrocarbon group which may optionally contain heteroatoms and/or be substituted, and also hydrocarbon groups which are bound to the basic skeleton via oxygen or nitrogen and which may likewise optionally contain heteroatoms and/or be substituted.

The heteroatoms are selected in particular from O, S, N, P, Si, Se, F, Cl, Br and/or I. The radicals R1 to R7 or R' or R" preferably each have 0 to 50, in particular 0 to 10, and even more preferably 0 to 5 heteroatoms. In some embodiments, the radicals R1 to R7 or R' or R" each have at least 1, in particular at least 2 heteroatoms. The heteroatoms may exist in the skeleton or as part of substituents. In one embodiment, the radicals R1 to R7 or R' or R" are each a hydrocarbon group which has one or more functional groups. Suitable functional groups are for example halogen, in particular F, Cl, Br or I, alkyl, in particular C1 to C20, even more preferably C1 to C6 alkyl, aryl, O-alkyl, O-aryl, S-aryl, S-alkyl, P-alkyl2, P-aryl2, N-alkyl2 or N-aryl2 or other donor or acceptor groups. In many cases, it is preferred that at least one of the radicals R1 to R7 or R' or R" contains at least one fluorine in order to increase the volatility of the complex.

Preferably, a hydrocarbon group here is an alkyl, alkenyl, alkynyl, aryl or heteroaryl group. In a further preferred embodiment, at least one of the radicals R1 to R7 is O—R' or N—R'R", R' once again being a hydrocarbon group which may contain one or more heteroatoms. Preferably, R' is alkyl, aryl, heteroaryl which may optionally contain one or more functional groups, as specified above. R" is H or has one of the meanings defined for R'. Most preferably, R1 to R7 are one or more residues of H, phenyl, t-butyl, COO-ethyl or O-ethyl.

However, in the complexes according to the invention, it is also possible that two or more radicals from R1 to R7 together form a fused ring system.

Unless specified otherwise, the expression alkyl or alk-, as used herein, preferably refers independently in each case to a C1-C20, in particular a C1-C5 hydrocarbon group. The expression aryl—preferably refers to an aromatic system with 5 to e.g. 20 C atoms, in particular with 6 to 10 C atoms, it optionally being possible for C atoms to be replaced by heteroatoms (e.g. N, S, O).

The complex furthermore contains ligand L1 or ligands L1, L2 and L3. L1, L2 and L3 independently of one another are each negatively charged or neutral ligands, preferably halogens, in particular chloride or bromide, or pseudohalogens, in particular thiocyanate, cyanate or cyanide. Preference is also given to ligands L1, L2 or L3 which are bound to the central atom via an element from group 16 of the Periodic Table, in particular via oxygen or sulphur, (e.g. alkoxides or thiolates), preferably O—R' or S—R', it being possible for R' to have the meanings specified in this regard.

In a further embodiment, preference is given to ligands which are bound via an element from group 15 of the Periodic Table, in particular via nitrogen, phosphorus or arsenic (e.g. nitrites, amines, phosphanes, arsanes), in particular NR'R", PR'R" or AsR'R", or via an element from group 14, in particular carbon, (e.g. cyanide, isonitriles, acetylides (C≡C)nR8, wherein n=1-10 and R8=alkyl or aryl, optionally substituted, tri(alkyl)silyl). In the case of coordination numbers greater than 4, the ligands L1-3 may be bound independently of one another or with one another, i.e. may be multidentate. The multidentate ligands may again be neutrally or negatively charged. Preference is given for example to bis- or tris(pyrazolyl)borate as negatively charged ligands or bis- and tris(phosphanes), diimines, etc. as examples of neutral ligands. Preferably, L1, L2 and L3 together form a ligand

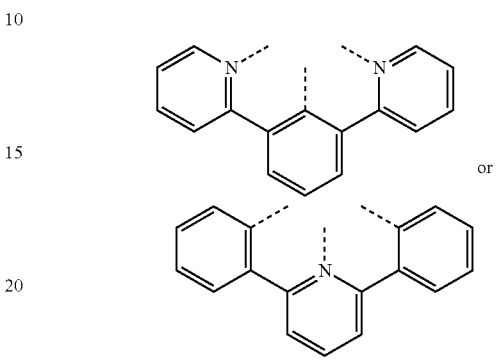

or

In one preferred embodiment, L1, L2 and L3 together in turn form a ligand of formula (III).

Particular preference is given to the complexes: 5,5'-di-tert-butyl-2,2'-m-phenylene-bis-oxazole-2-platinum(II)bromide; 5,5'-diphenyl-2,2'-m-phenylene-bis-oxazole-2-platinum(II)bromide; 2,6-bis(5-ethoxyoxazol-2-yl)phenyl-bromoplatinum(II); 2-(4-methoxycarbonyloxazol-2-yl)-6-(5-ethoxyoxazol-2-yl)phenyl-bromoplatinum(II); (3-oxo-3-ethoxypropynyl)-[2,6-bis(5-ethoxyoxazol-2-yl)phenyl]-platinum(II); (3-hydroxylpropynyl)-[2,6-bis(5-ethoxyoxazol-2-yl)phenyl]-platinum(II); 5,5'-di-tert-butyl-2,2'-m-phenylene-bis-oxazole-2-palladium(II)bromide; 5,5'-diphenyl-2,2'-m-phenylene-bis-oxazole-2-palladium(II) bromide; and

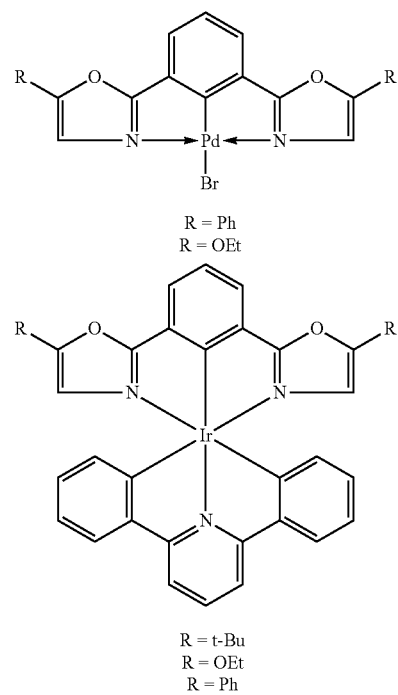

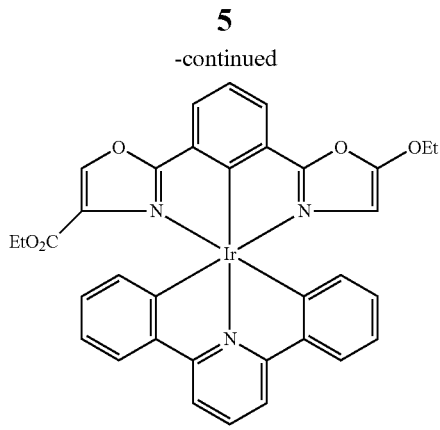

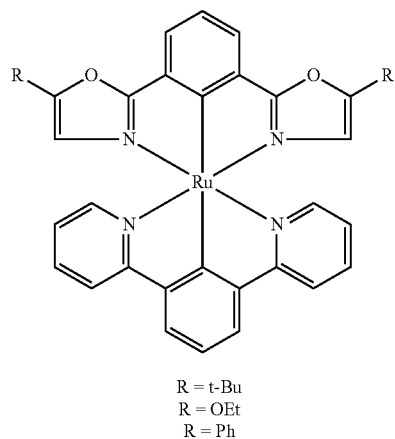

R = t-Bu
R = OEt
R = Ph

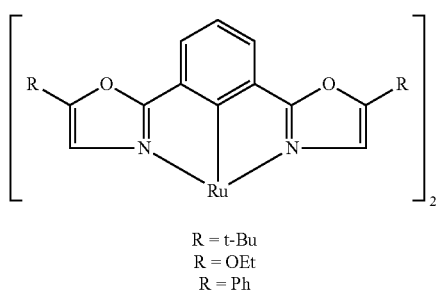

R = t-Bu
R = OEt
R = Ph

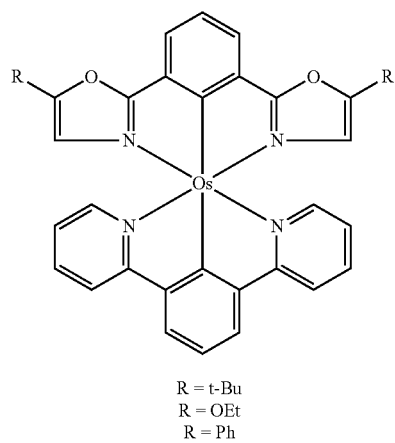

R = t-Bu
R = OEt
R = Ph

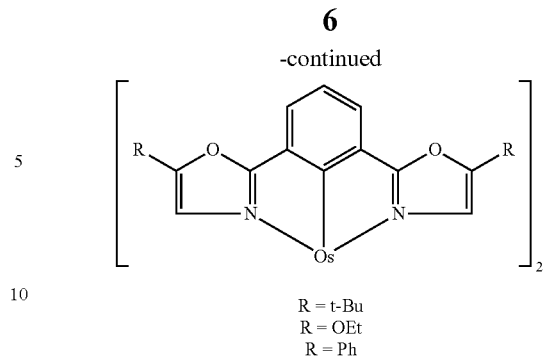

R = t-Bu
R = OEt
R = Ph

The compounds according to the invention have completely new molecular structures with a tridentate ligand/metal bond. The complexes according to the invention comprising trivalent chelate ligands are in particular thermally very stable. They are therefore highly suitable for sublimation from the technical point of view.

The invention also relates to compounds of formula (IV)

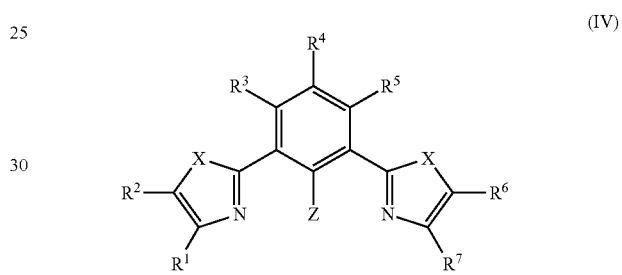

(IV)

in which X and R1 to R7 are as defined herein, and Z is a leaving group, in particular H or halogen, e.g. F, Cl, Br or J, preferably Br.

These compounds are particularly suitable as ligands. Complexes comprising ligands of formula III formed from compounds of formula (IV) are thermally stable due to the trivalency thereof.

Particular preference is given to the following compounds of formula (IV)

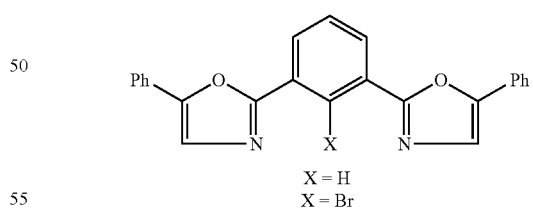

X = H
X = Br

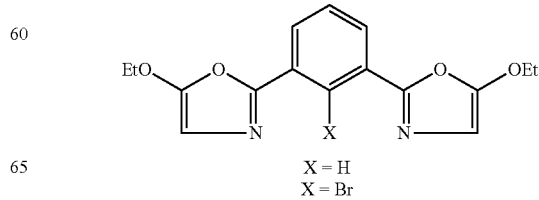

X = H
X = Br

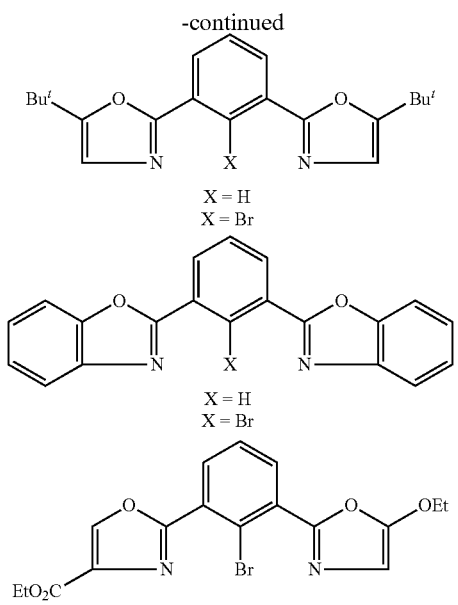

X = H
X = Br

X = H
X = Br

It has surprisingly been found that, through the use according to the invention of the complexes of formula (I) or (II) in the emitter layer, it is possible to obtain light-emitting devices which have excellent properties. The compounds of formula (I) or (II) used according to the invention are in particular stable with respect to sublimation and are therefore suitable for the production of OLEDs by means of vacuum deposition. Furthermore, when used as emitters in OLEDs, they exhibit an electrophosphorescence with high efficiency and brightness. In particular, the compounds used according to the invention exhibit high quantum yields. The complexes can moreover be varied through substitution or/and variation of the ligands, resulting in many possibilities for modifying and controlling the emission properties (e.g. color, quantum yield, decay time, etc.).

The mode of operation of one embodiment of the light-emitting devices according to the invention is shown schematically in FIG. 1. The device comprises at least one anode, one cathode and one emitter layer. Advantageously, one or both of the electrodes used as the cathode or anode is of transparent design, so that the light can be emitted through this electrode. Preferably, indium tin oxide (ITO) is used as the transparent electrode material. With particular preference, a transparent anode is used. The other electrode may likewise be formed from a transparent material, but may also be formed from another material with a suitable electron work function if light is to be emitted only through one of the two electrodes. The second electrode, in particular the cathode, preferably consists of a metal with a low electron work function and good electrical conductivity, for example aluminum, or silver, or an Mg/Ag or Ca/Ag alloy. An emitter layer is arranged between the two electrodes. This emitter layer may be in direct contact with the anode and the cathode, or in indirect contact, indirect contact meaning that further layers are contained between the cathode or anode and the emitter layer so that the emitter layer and the anode or/and cathode do not touch one another but rather are in electrical contact with one another via further intermediate layers. When a voltage is applied, for example a voltage of 2-20 V, in particular of 5-10 V, negatively charged electrons leave the cathode, for example a conductive metal layer, e.g. an aluminum cathode, and migrate in the direction of the positive anode. From this anode in turn, positive charge carriers, so-called holes, migrate in the direction of the cathode. According to the invention, the metal-organic complexes of formula (I) and (II) are located as emitter molecules in the emitter layer arranged between the cathode and the anode. The migrating charge carriers, i.e. a negatively charged electron and a positively charged hole, recombine at the emitter molecules or in the vicinity thereof and lead to neutral but energetically excited states of the emitter molecules. The excited states of the emitter molecules then release their energy as light emission.

If the emitter materials are capable of sublimation, the light-emitting devices according to the invention can be produced via vacuum deposition. Alternatively, a build-up via wet-chemical application is also possible, for example via spin-coating methods, via inkjet printing or via screen printing methods. The structure of OLED devices is described in detail for example in US2005/0260449 A1 and in WO 2005/098988 A1.

The light-emitting devices according to the invention can be manufactured by means of the vacuum sublimation technique and may contain a plurality of further layers, in particular an electron injection layer and an electron transport layer (e.g. Alq3=Al-8-hydroxyquinoline or B-Alq=Al-bis(2-methyl-8-hydroxyquinolato)-4-phenylphenolate) and/or a hole injection (e.g. CuPc) and hole transport layer or a hole transport layer (e.g. α-NPD). However, it is also possible that the emitter layer performs functions of the hole or electron transport layer (suitable materials are explained on pages 7/8).

The emitter layer preferably consists of an organic matrix material with a sufficiently large singlet S0-triplet T1 energy gap for the respective emission color (T1 position), e.g. of UGH, PVK (polyvinylcarbazole), CBP (4,4'-bis(9-carbazolyl)biphenyl) or other matrix materials. The emitter complex is preferably incorporated in this matrix material by doping, e.g. preferably in a proportion of 1 to 10% by weight.

The emitter layer may also be formed without a matrix, by applying the appropriate complex as 100% material. Such an embodiment is described further below.

In one particularly preferred embodiment, the light-emitting device according to the invention also has a CsF intermediate layer between the cathode and the emitter layer or an electron transport layer. This intermediate layer has in particular a thickness of 0.5 nm to 2 nm, preferably of approximately 1 nm. This intermediate layer mainly brings about a reduction in the electron work function.

Furthermore, the light-emitting device is preferably applied to a substrate, for example to a glass substrate.

In one particularly preferred embodiment, an OLED structure for an emitter according to the invention which is capable of sublimation comprises, in addition to an anode, emitter layer and cathode, also at least one, in particular a plurality and particularly preferably all of the layers mentioned below and shown in FIG. 2.

The entire structure is preferably located on a substrate material, it being possible to use for this in particular glass or any other solid or flexible transparent material. The anode, for example an indium tin oxide (ITO) anode, is arranged on the substrate material. A hole transport layer (HTL), for example α-NPD (N,N'-diphenyl-N,N'-bis(1-methyl)-1,1'-biphenyl-4,4'-diamine), is arranged on the anode and between the emitter layer and the anode. The thickness of the hole transport layer is preferably 10 to 100 nm, in particular 30 to 50 nm. There may be arranged, between the anode and the hole transport layer, further layers which improve hole injection, e.g. a copper phthalocyanine (CuPe) layer. This layer has a thickness of preferably 5 to 50, in particular 8 to 15 nm. Applied to the hole transport layer and between the hole transport layer and the emitter layer there is preferably an electron blocking layer which ensures that the electron transport to the anode is suppressed, since such a flow would only cause ohmic losses. The thickness of this electron blocking layer is preferably 10 to 100 nm, in particular 20 to 40 nm. This additional layer can be omitted in particular if the HTL layer is already intrinsically a poor electron conductor.

The next layer is the emitter layer which contains or consists of the emitter material according to the invention. In the embodiment using emitters capable of sublimation, the emitter materials are preferably applied by sublimation. The layer thickness is preferably between 40 nm and 200 nm, in particular between 70 nm and 100 nm. The emitter material according to the invention may also be applied by vapor co-deposition together with other materials, in particular with matrix materials. For emitter materials according to the invention which emit in green or red, customary matrix materials such as CBP (4,4'-bis(N-carbazolyl)biphenyl) are suitable. However, for complexes of formula (I), it is also possible to build up a 100% emitter material layer. For emitter materials according to the invention which emit in blue, use is preferably made of UGH matrix materials (cf. M. E. Thompson et al., Chem. Mater. 2004, 16, 4743). In order to produce light of mixed color when using compounds according to the invention with different metal central ions, vapor co-deposition can likewise be used.

There is preferably applied to the emitter layer a hole blocking layer which reduces ohmic losses that might be caused by hole flows to the cathode. This hole blocking layer has a thickness of preferably 10 to 50 nm, in particular 15 to 25 nm. A suitable material for this is for example BCP (4,7-diphenyl-2,9-dimethylphenanthroline, also known as bathocuproine). An ETL layer of electron transport material (ETL=electron transport layer) is preferably applied to the hole blocking layer and between this layer and the cathode. This electron transport layer preferably consists of Alq3 which can be applied by vapor deposition and which has a thickness of 10 to 100 nm, in particular 30 to 50 nm. An intermediate layer, for example of CsF or LiF, is preferably applied between the ETL layer and the cathode. This intermediate layer reduces the electron injection barrier and protects the ETL layer. This layer is usually applied by vapor deposition. The intermediate layer is preferably very thin, in particular with a thickness of 0.5 to 2 nm, more preferably 0.8 to 1.0 nm. Finally, a conductive cathode layer is applied by vapor deposition, in particular with a thickness of 50 to 500 nm, more preferably 100 to 250 nm. The cathode layer preferably consists of Al, Mg/Ag (in particular in a ratio of 10:1) or other metals. Voltages of between 3 and 15 V are preferably applied to the described OLED structure for an emitter according to the invention which is capable of sublimation.

The OLED device may also be manufactured partially via a wet chemical process, namely for example according to the following structure: glass substrate, transparent ITO layer (of indium tin oxide), e.g. PEDOT/PSS (e.g. 40 nm), 100% complex of formula (I) according to the invention (e.g. 10 to 80 nm) or complexes of formula (I) or formula (II) incorporated by doping (e.g. 1%, in particular 4% to 10%) in a suitable matrix (e.g. 40 nm), vapor-deposited Alq3 (e.g. 40 nm), vapor-deposited LiF or CsF protective layer (e.g. 0.8 nm), vapor-deposited metal cathode Al or Ag or Mg/Ag (e.g. 200 nm).

With particular preference, an OLED structure for a soluble emitter according to the invention has the structure described below and shown in FIG. 3, but comprises at least one, more preferably at least two and most preferably all of the layers mentioned below.

The device is preferably applied to a substrate material, in particular to glass or another solid or flexible transparent material. An anode, for example an indium tin oxide anode, is applied to the substrate material. The layer thickness of the anode is preferably 10 nm to 100 nm, in particular 30 to 50 nm. Applied to the anode and between the anode and the emitter layer is an HTL layer (hole transport layer) made from a hole transport material, in particular from a hole transport material which is water-soluble. Such a hole transport material is for example PEDOT/PSS (polyethylenedioxythiophene/polystyrenesulphonic acid). The layer thickness of the HTL layer is preferably 10 to 100 nm, in particular 40 to 60 nm. Next, the emitter layer (EML) is applied, which contains a soluble emitter according to the invention. The material may be dissolved in a solvent, for example in acetone, dichloromethane or acetonitrile. It is thus possible to prevent any dissolution of the underlying PEDOT/PSS layer. The emitter material according to the invention may be used in a low concentration, e.g. 2 to 10% by weight, for complexes of formula (I) and formula (II), but also in a higher concentration or as a 100% layer for complexes of formula (I). It is also possible to apply the emitter material with high or medium doping in a suitable polymer layer (e.g. PVK=polyvinylcarbazole). When exploiting the metal/metal interaction using the complex of formula (I), the doping concentration is preferably so high that a dimer, trimer or oligomer formation of the emitter can take place.

A layer of electron transport material is preferably applied to the emitter layer, in particular with a layer thickness of 10 to 80 nm, more preferably 30 to 50 nm. A suitable material for the electron transport material layer is for example Alq3, which can be applied by vapor deposition. Next, preferably a thin intermediate layer is applied, which reduces the electron injection barrier and protects the ETL layer. This intermediate layer preferably has a thickness of between 0.5 and 2 nm, in particular between 0.5 and 1.0 nm and preferably consists of CsF or LiF. This layer is usually applied by vapor deposition. For a further simplified OLED structure, optionally the ETL layer and/or the intermediate layer may be omitted.

Finally, a conductive cathode layer is applied, in particular by vapor deposition. The cathode layer preferably consists of a metal, in particular Al or Mg/Ag (in particular in a ratio of 10:1).

Voltages of 3 to 15 V are preferably applied to the device.

It is essential to the invention that the light-emitting device contains as the emitter at least one M-oxazole complex of formula (I) or (II), in particular a complex in which X=O.

It has been found according to the invention that compounds of formula (I) or (II) are highly suitable as emitter molecules for light-emitting devices and in particular for organic light-emitting devices (OLEDs). The compounds according to the invention are highly suitable in particular for use in light-producing systems, such as for example displays or lighting devices.

The use of M-oxazole complexes of formula (I) or (II) as emitter materials in OLEDs results in a number of advantages. For example, emitter layers can be produced by sublimation. Due to the trivalency of the oxazole ligand on the metal, the emitter complexes are particularly stable, even under the relatively hard sublimation conditions required for technological manufacture. In the case of using 100% or highly concentrated emitter layers with materials of formula (I) according to the invention, no concentration fluctuations can occur during manufacture of the devices. Furthermore, it is possible to provide the emitter in crystalline layers or in oligomer layers. In these systems, particularly in crystalline layers of complexes of formula (I), the charge carrier mobilities are much higher than in amorphous layers. Furthermore, with the emitter molecules according to the invention, high light densities can be achieved at high current densities. Moreover, a relatively high efficiency (quantum efficiency) can also be achieved at high current densities. The complexes of formulae (I) and (II) can also be used according to the invention when dissolved in suitable matrices with low doping (e.g. 2-10%).

In one embodiment of the invention, the complexes of formula (I) according to the invention can advantageously be used in high concentration in the emitter layer. The proportion of complexes of formula (I) in the emitter layer is in this case preferably more than 80% by weight, in particular more than 90% by weight, even more preferably more than 95% by weight and in particular 100% by weight, relative to the total weight of the emitter layer. At such high concentrations, oligomers are formed which then act as oligomer emitters. The transitions which lead to the emission are based here on metal/metal interactions between the individual metal atoms of the complexes in the oligomers. Depending on the doping amount and as a function of the radicals R, the compounds of formula (I) according to the invention in such emitter layers exhibit different M-M gaps, as a result of which the emission colors can vary over wide ranges.

In a further preferred embodiment, the complexes of formula (I) are used in medium concentrations in the emitter layer, so that monomers and oligomers exist next to one another. As a result, it is possible to achieve a mixed-color emission, e.g. white. The proportion of complexes of formula (I) in the emitter layer is in this case preferably more than 10% by weight, in particular more than 20% by weight, even more preferably more than 30% by weight and in particular more than 40% by weight and up to 80% by weight, in particular up to 70% by weight, more preferably up to 60% by weight, in each case relative to the total weight of the emitter layer.

In a further preferred embodiment of the invention, complexes of formula (I) or/and of formula (II) are used in low concentration in the emitter layer, as a result of which a monomer emission is achieved in the OLED device. The complexes of formula (I) or/and (II) are in this case present in the emitter layer in a proportion of more than 2% by weight, in particular more than 4% by weight and up to 10% by weight, in particular up to 8% by weight, relative to the total weight of the emitter layer.

In a further preferred embodiment, according to the invention at least two different complexes of formula (I) or (II) are used in the light-emitting device. By virtue of such emitter layers containing a plurality of complexes, in particular light of mixed color can be obtained. Preferably, the emitter layer comprises at least one complex of formula (I) where M=Pt and at least one complex of formula (I) where M=Pd. Particular preference is given to emitter layers which have a high concentration of compounds where M=Pd(II), doped in a low concentration with complexes of formula (I) where M=Pt(II). The incorporation of Pt complexes in Pd complex emitter layers, in particular emitter layers in which Pd complex oligomers exist, leads to mixed-color light of the OLED devices.

In one preferred embodiment, the emitter layer contains complexes of formula (I) and formula (II) in a concentration of more than 1% by weight, relative to the total weight of the emitter layer, in particular more than 2% by weight, more preferably more than 5% by weight and up to 10% by weight, in particular up to 8% by weight. However, it is also possible to provide emitter layers which contain almost completely complexes of formula (I) and in particular >80% by weight and most preferably >90% by weight, in particular >95% by weight, more preferably >99% by weight. In a further embodiment, the emitter layer consists completely, i.e. 100%, of complexes of formula (I). When using the complexes according to the invention in high concentration in the emitter layer, crystalline layers or stacks of the complexes with relatively short metal-metal gaps form. In these stacks, strong electronic interactions occur. The emission wavelength is in this case defined by the M-M gap. The use of highly concentrated emitter layers and in particular of crystalline or quasi-crystalline layers offers further advantages. In particular, no concentration fluctuations occur during manufacture or else these have only a slight effect in highly concentrated systems. Furthermore, when crystalline layers are formed, the charge carrier mobilities, i.e. the electron and hole mobilities, are much higher than in amorphous layers. Furthermore, with such concentrated emitter layers, a high light density and a high efficiency, i.e. a high quantum efficiency, can be achieved at high current densities.

In particular, the efficiency and the durability of OLED devices can be increased due to the high charge carrier mobility of oligomer, or crystalline, or quasi-crystalline layers of complexes of formula (I).

The present invention provides inter alia the following advantages: Completely new molecular structures with tridentate ligand-metal binding; more efficient and brighter emitters by limiting the molecule flexibility; control of the emission colors from green to red by means of substitutions; high thermal stability; good capability for sublimation and thus good suitability for technical use using the method of vacuum vapor deposition; high long-term stability; high chemical stability with respect to oxygen and water; extremely high chemical variability; good solubility and thus highly suitable for doping for spin-coating or inkjet printing methods in different polymer matrix materials (good incorporation in the emitter layer); good suitability for chemical linking to polymers, functionalization of polymers for use in spin coating, inkjet printing, etc.

The complexes used as emitters according to the invention can be adapted easily (by selecting suitable matrix materials) and in particular by selecting electron-attracting or electron-repelling substitutents in the wavelength range.

Preferably, use is made of compounds which exhibit emission at a temperature of >20° C. and at temperatures of particularly preferably more than 100° C.

The invention also relates to the use of a compound of formula (I) or (II), as defined herein, as the emitter in a light-emitting device, in particular in an organic light-emitting device.

BRIEF DESCRIPTION OF THE DRAWINGS

The invention will be further explained by the appended figures and the following examples.

FIG. 1 shows an example of an OLED device which can be produced by vacuum sublimation and contains complexes according to the invention.

FIG. 2 shows an example of a differentiated highly efficient OLED device which contains emitter materials capable of sublimation according to the invention.

FIG. 3 shows an example of an OLED device for emitters according to the invention which are to be applied via a wet chemical process. The layer thickness information is given by way of example.

EXAMPLES

Figure 4:
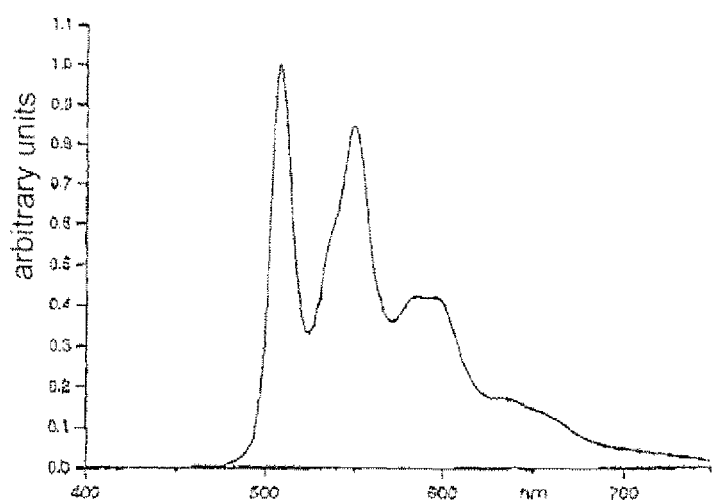
FIG. 4 shows the emission spectrum of platinum complex A. The conditions were as follows: excitation: 390.4 nm, slits: 3.5/3.5 1.0 nm 0.3 s: solution in CHCl3; temperature: 300 K; 20 min argon saturated; Riter: KV 450.
Figure 5:
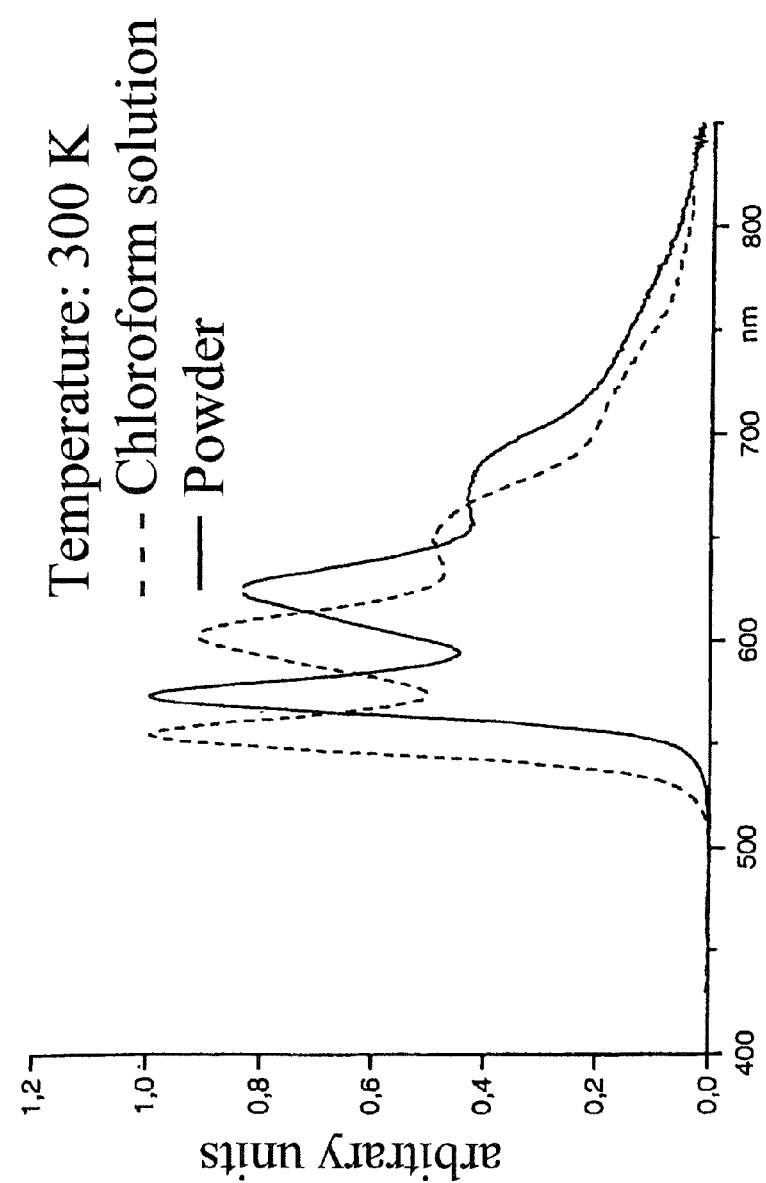
FIG. 5 shows the luminescence spectrum of platinum complex B measured in CHCl3 ($\lambda$ex=415 nm) and as a solid ($\lambda$ex=390 nm).
Figure 6A:
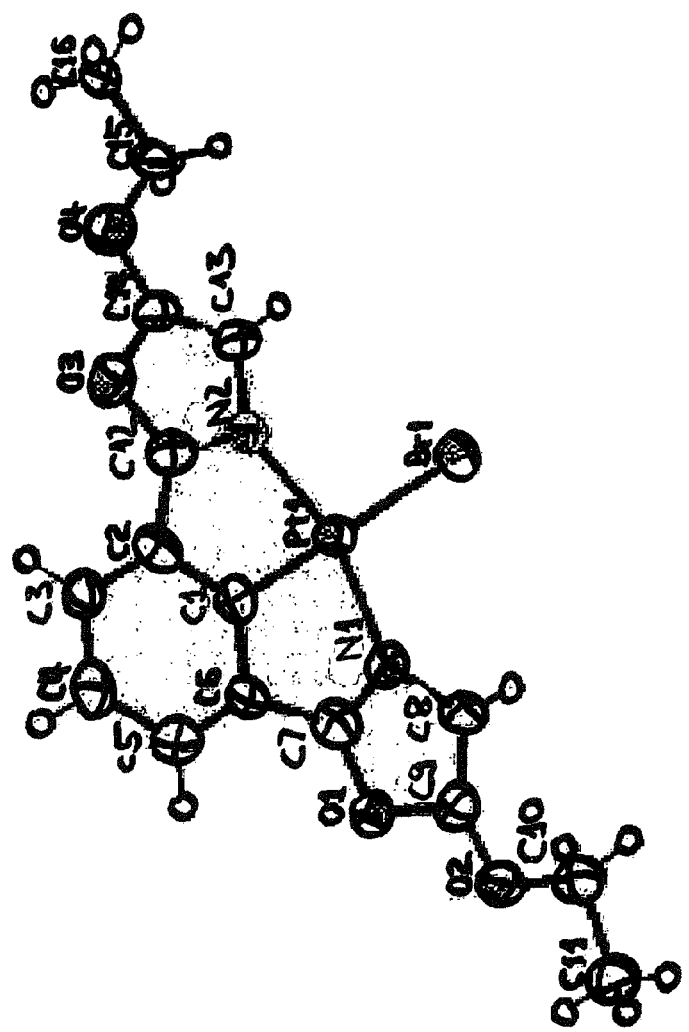
FIG. 6a shows the structure of platinum complex C.
Figure 6B:
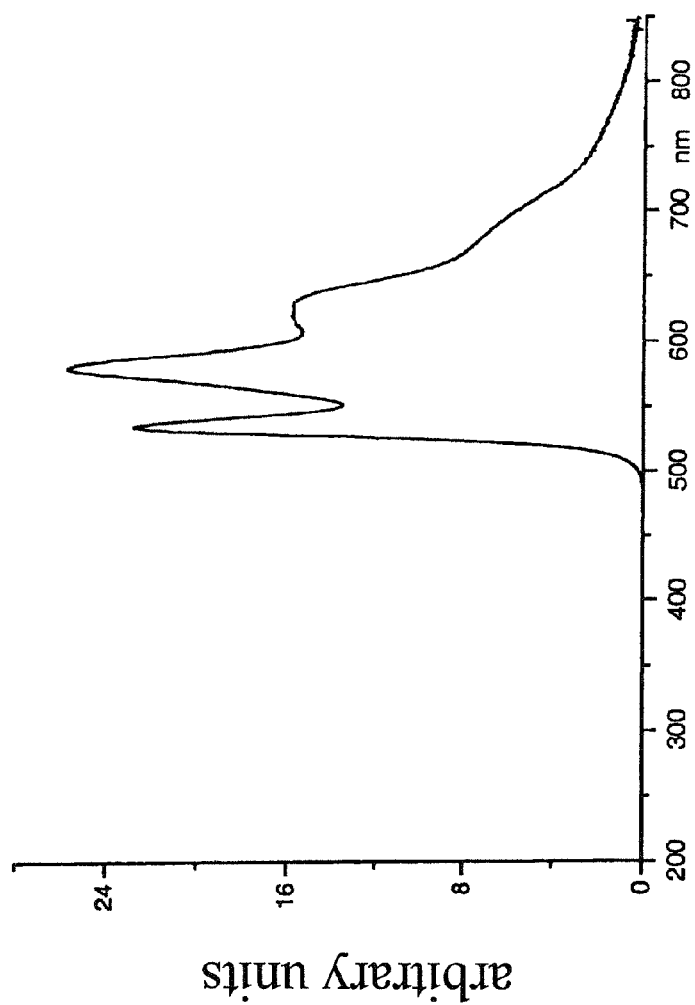
FIG. 6b shows the emission spectrum of platinum complex C. The conditions were as follows: excitation: 370 nm; 0.5 nm, 25/2.5 0.3; solution in EtOH, 300 K; filter: WG 420.
Figure 7A:
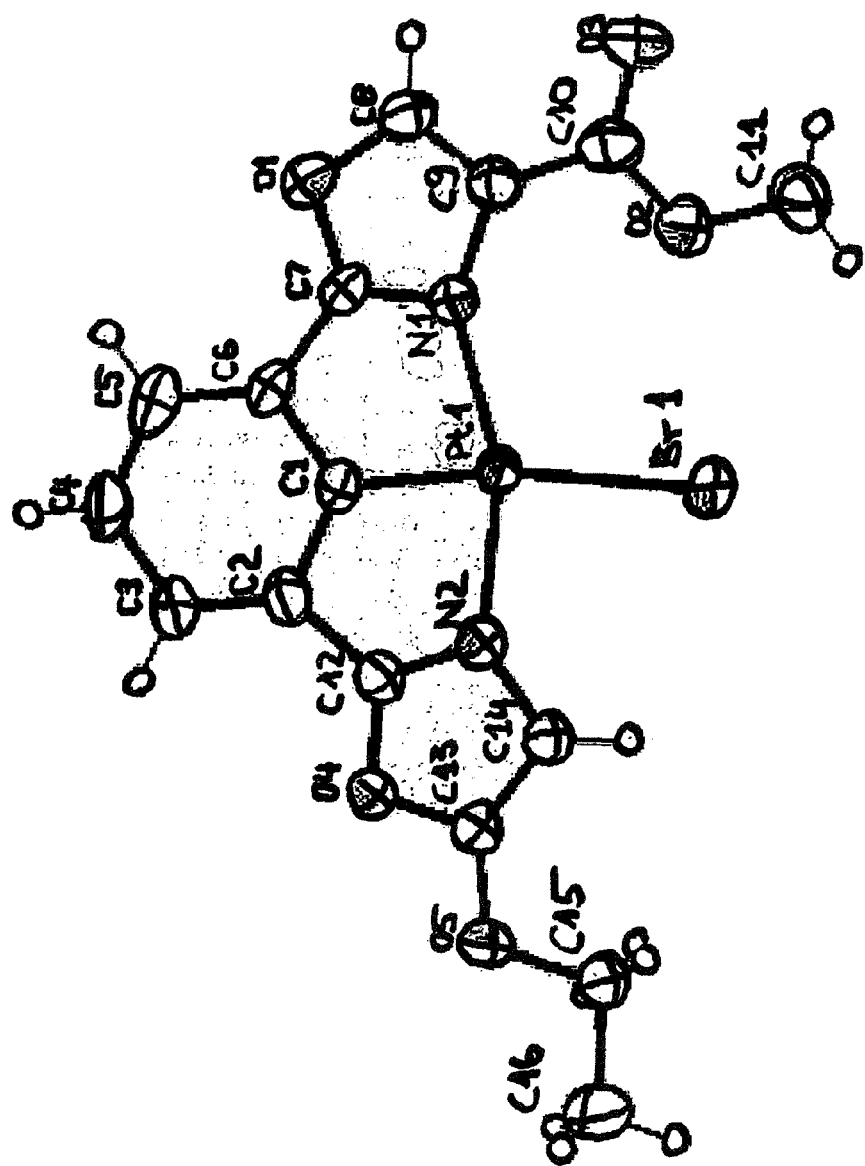
FIG. 7a shows the structure of platinum complex D.
Figure 7B:
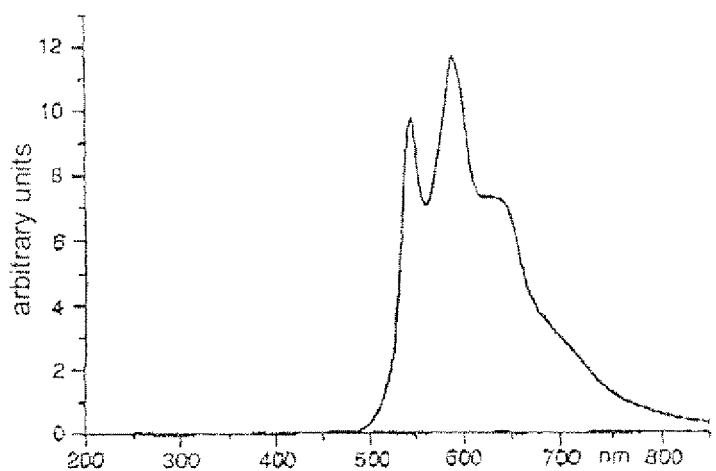
FIG. 7b shows the emission spectrum of platinum complex D. The conditions were as follows: excitation: 370 nm; 0.5 nm, 2.5/2.5 0.3; solution in EtOH, 300 K; filter: WG 420.
Figure 8:
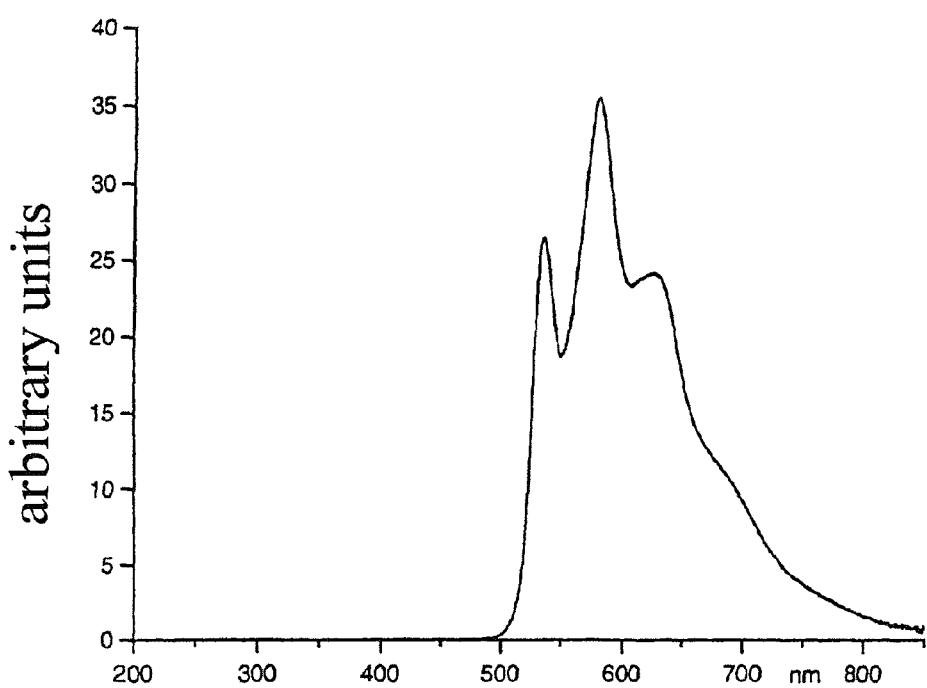
FIG. 8 shows the emission spectrum of platinum complex E. The conditions were as follows: excitation: 370 nm; 0.5 nm, 3/3 0.3; solution in EtOH, 300 K; filter: WG 420; 20 min Ar saturated.

1. Platinum Complex A 5,5'-Di-tert-butyl-2,2'-m-phenylene-bis-oxazole-2-platinum(II)bromide (A)

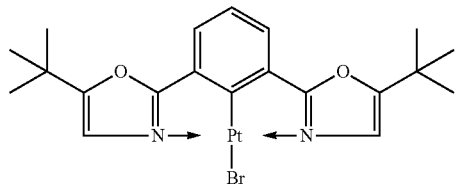

(A)

Pt2(dipdba)3 (161 mg, 0.12 mmol, 1.6 eq "Pt") was added under a dinitrogen atmosphere to a solution of 2-bromo-1,3-di[2-(5-tert-butyloxazolyl)]benzene (60 mg, 0.15 mmol, 1.0 eq) in 3 ml of THF. The reaction mixture was stirred overnight (20 h) at 60° C. The mixture was concentrated in vacuo in order to obtain the crude material. By means of column chromatography (SiO2, 2×24 cm. hexane/EtOAc 3:1), A was obtained as an orange solid (77 mg, 0.13 mmol, 86%).

Rf (SiO2, hexane/EtOAc 3:1)=0.30 (UV); M.p.>295° C. (decomp.); 1H-NMR (300 MHz, CDCl3): $\delta$=7.52-7.43 (m, 2H), 7.31-7.18 (m, 3H), 1.38 (s, 18H); 13C-NMR (75.5 MHz, CDCl3): $\delta$=172.2, 162.0, 157.3, 128.0, 123.3, 123.0, 119.8, 32.2, 28.4; IR (KBr): 3140, 3060, 2970, 2870, 1590, 1520, 1460, 1430, 1395, 1365, 1320, 1280, 1210, 1150, 1130, 1110, 1025, 1005, 940, 815, 720, 680 cm−1; MS (PI-FDMS): m/z (%)=1117.1 (40) [2M+−Br], 598.4 (100) [M+]; C20H23BrN2O2Pt (598.39): calculated C, 40.14; H, 3.87; N, 4.68; found C, 40.34; H, 3.90; N, 4.74.

2. Platinum Complex B 5,5'-Diphenyl-2,2'-m-phenylene-bis-oxazole-2-platinum(II)bromide (B)

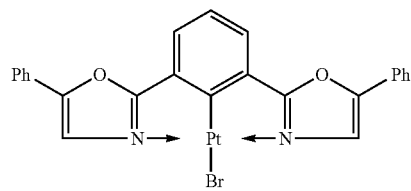

(B)

Pt2(dipdha)3 (86 mg, 0.064 mmol, 1.6 eq "Pt") was added under a dinitrogen atmosphere to a solution of 2-bromo-1,3-di[2-(5-phenyloxazolyl)]benzene (35 mg, 0.079 mmol, 1.0 eq) in 2 ml of THF. The reaction mixture was stirred overnight (20 h) at 60° C. A precipitation and a gas development were observed. After the reaction time, CH2Cl2 was added to the mixture. Through filtration, the crude product was obtained, which was recrystallized from CHCl3/Et2O to give 23 mg (0.036 mmol, 45%) of B as a dark yellow solid. Assignment of the product peak in the 1H-NMR spectrum was again not possible.

M.p.>420° C. (decomp.); IR (KBr): 3160, 3070, 1590, 1570, 1515, 1490, 1455, 1400, 1365, 1325, 1252, 1210, 1160, 1135, 1010, 935, 810, 760, 725, 685 cm−1: MS (PI-FDMS): m/z (%)=1197.6 (60) [2M+−Br], 638.6 (100) [M+]: C24H15BrN2O2Pt (638.37): calculated C, 45.16; H, 2.37; N, 4.39; found C, 44.48; H, 2.55; N, 4.25.

3. Platinum Complex C 2,6-Bis-(5-ethoxyoxazol-2-yl)phenyl bromoplatinum(II)

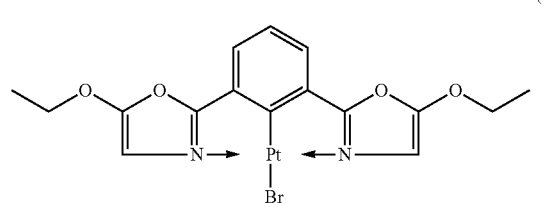

(C)

1H NMR (300 MHz, CDCl3): $\delta$=7.31-7.25 (m, 2H), 7.16 (dd, J=6.9, 8.5 Hz, 1H), 6.67 (s, satellite JPt—H=9.2 Hz, 2H), 4.26 (q, J=7.0 Hz, 4H), 1.50 (t, J=7.1 Hz, 6H).

13C NMR (75 MHz, CDCl3): $\delta$=164.6, 159.0, 157.2, 128.1, 123.4, 121.4 (satellite JPt—C=18.7 Hz), 100.2 (satellite JPt—C=21.3 Hz), 67.0, 14.5.

MS (FI-FDMS): m/z (%)=1147.3 (41) [2M+], 1068.6 (60) [2M+−HBr], 573.9 (100) [M+].

Elemental analysis: found C, 33.55; H, 2.48; N, 4.76; calculated C, 33.46; H, 2.63; N, 4.88.

4. Platinum Complex D 2-(4-Methoxycarbonyloxazol-2-yl)-6-(5-ethoxyoxazol-2-yl)phenyl bromoplatinum(II)

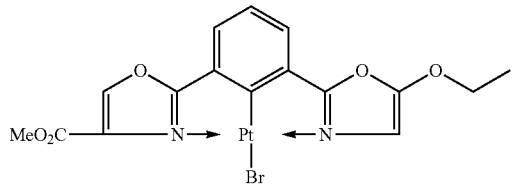

(D)

1H NMR (300 MHz, CD2Cl2): δ=8.25 (s, satellite JPt—H=3.4 Hz, 1H), 7.45 (d, J=7.7 Hz, Satellite JPt—H=3.2 Hz, 1H), 7.33 (d, J=6.7 Hz, satellite JPt—H=3.1 Hz, 1H), 7.16 (t, J=6.9 Hz, 1H), 6.82 (s, satellite JPt—H=10.5 Hz, 1H), 4.30 (q, J=7.0 Hz, 4H), 1.50 (t, J=7.1 Hz, 6H).

13C NMR (75 MHz, CD2Cl2): δ=175.4, 164.1, 159.5, 159.1, 156.6, 142.2 (satellite JPt—C=15.0 Hz), 134.2, 129.0, 126.8, 123.9, 123.6, 123.3 99.9 (satellite JPt—C=22.8 Hz), 70.5, 53.4, 14.7.

MS (FI-FDMS): m/z (%)=1176.0 (16) [2M+], 588.3 (100) [M+].

Elemental analysis: found C, 32.78; H, 2.18; M, 4.74; calculated C, 32.67; H, 2.23; N, 4.76.

5. Platinum Complex E (3-Oxo-3-ethoxypropynyl)-[2,6-bis(5-ethoxyoxazol-2-yl)phenyl]platinum(II)

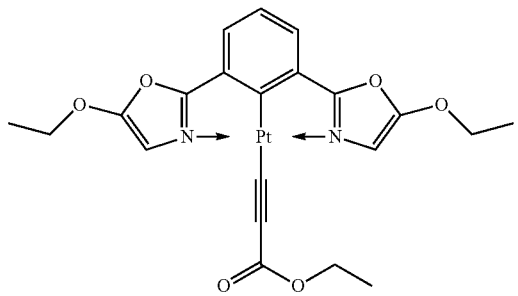

(E)

1H NMR (300 MHz, CDCl3): δ=7.35 (dd, J=7.4, 8.0 Hz, 2H), 7.16 (dd, J=7.1, 8.2 Hz, 1H), 6.62 (s, satellite JPt—H=9.6 Hz, 2H), 4.26 (q, J=7.1 Hz, 4H), 4.23 (q, J=7.2 Hz, 2H), 1.50 (t, J=7.1 Hz, 6H), 1.33 (t, J=7.1 Hz, 3H).

13C NMR (75 MHz, CDCl3): δ=172.2, 168.7, 158.9, 154.4, 129.8, 129.4, 124.2, 121.3, 121.2, 102.4 (satellite JPt—C=25.4 Hz), 69.7, 60.7, 14.5, 14.4.

LR MS (FI-FDMS): m/z=591.1 [M+].

6. Platinum Complex F (3-Hydroxylpropynyl)-[2,6-bis(5-ethoxyoxazol-2-yl)phenyl]platinum(II)

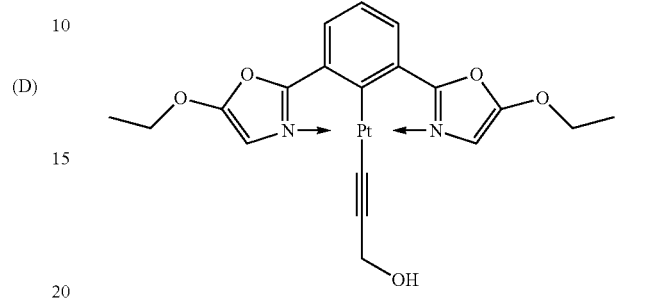

(F)

1H NMR (300 MHz, CDCl3): δ=7.37 (d, J=7.7 Hz, 2H), 7.16 (dd, J=7.4, 8.0H, 1H), 6.67 (s, satellite JPt—H=9.7 Hz, 2H), 4.62 (d, J=5.2 Hz, satellite JPt—H=7.8 Hz, 2H), 4.27 (q, J=7.0 Hz, 4H), 1.60 (br t, J=5.8 Hz, 1H), 1.50 (t, J=7.1 Hz, 6H).

7. Palladium Complex G 5,5'-Di-tert-butyl-2,2'-m-phenylene-bis-oxazole-2-palladium(II)bromide

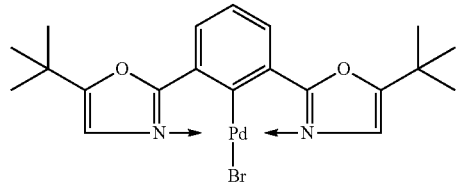

(G)

Pd(dba)2 (223 mg, 0.388 mmol, 1.0 eq) and 2-bromo-1,3-di-[2-(5-tert-butyloxazolyl)]-benzene (157 mg, 0.389 mmol, 1.0 eq) were dissolved in dry benzene (14 ml). The solution was degassed (3×freezing/pumping/thawing cycles) and heated at reflux until the purple color had faded (20 min). The reaction mixture was concentrated in vacuo, as a result of which the crude material was obtained. By means of column chromatography (SiO2, 3×20 cm, hexane/EtOAc 3:1), G (166 mg, 0.326 mmol, 84%) was obtained as a yellow solid.

Rf (SiO2, hexane/EtOAc 3:1)=0.18 (UV); M.p.>290° C. (decomp.); 1H-NMR (300 MHz, MeOH-d4): δ=7.25-7.20 (m, 2H), 7.12 (dd, 1H, J=8.5, 6.6 Hz), 6.89 (s, 2H), 1.42 (s, 18H); 13C-NMR (75.5 MHz, MeOH-d4): δ=168.6, 164.7, 162.7, 131.0, 126.0, 123.9, 121.0, 33.1, 29.0; IR (KBr): 3137, 3058, 2966, 2906, 2870, 2369, 1591, 1459, 1397, 1364, 1281, 1211, 1152, 1126, 1030, 1004, 946, 824, 724, 681 cm−1; MS (PI-FDMS): m/z (%)=939.5 (50) [2M+−Br], 510.4 (100)

[M+], 429.4 (20) [M+–Br]; C20H23BrN2O2Pd (509.73); calculated C, 47.13; H, 4.55; N, 5.50; found C, 46.99; H, 4.68; N, 5.44.

8. Palladium Complex H 5,5'-Diphenyl-2,2'-m-phenylene-bis-oxazole-2-palladium(II)bromide

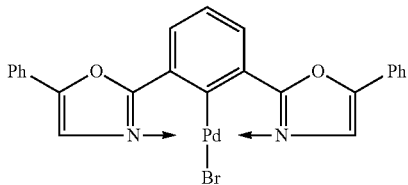

(H)

Pd(dba)2 (115 mg, 0.200 mmol, 1.0 eq) and 2-bromo-1,3-di[2-(5-phenyloxazolyl)]-benzene (88.6 mg, 0.200 mmol, 1.0 eq) were dissolved in dry benzene (7 ml). The solution was degassed (3×freezing/pumping/thawing cycles) and heated at reflux until the purple color had faded (20 min). A white to grey precipitation was observed. The reaction mixture was concentrated in vacuo. The addition of CH2Cl2 and filtration of the resulting mixture produced a grey insoluble filter cake (67 mg) and a yellow filtrate. The filtrate was concentrated to a smaller volume and, when Et2O was added, the product began to precipitate. This crude product was recrystallized from CH2Cl2/Et2O to give 23 mg (0.042 mmol, 21%) of H as a yellow loose solid. Assignment of the product peak in the 1H-NMR spectrum was not possible.

M.p.>400° C. (decomp.); IR (KBr): 3143, 3051, 2373, 1589, 1524, 1487, 1452, 1389, 1318, 1250, 1201, 1155, 1130, 1004, 932, 813, 760, 726, 688 cm-1; MS (PI-FDMS): m/z (%)=1019.1 (25) [2M+–Br], 550.2 (100) [M+], 468.5 (60) [M+–Br], 444.3 (40) [M+–Pd], C24H15BrN2O2Pd (549.71): calculated C, 52.44; H, 2.75; N, 5.10; found C, 52.36; H, 2.95; N, 5.11.

The invention claimed is:

1. A complex of formula (I) or (II):

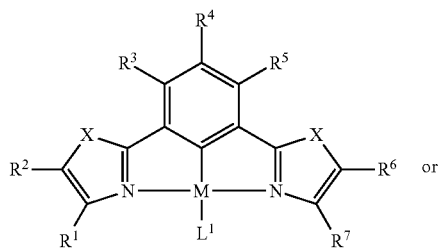

(I)

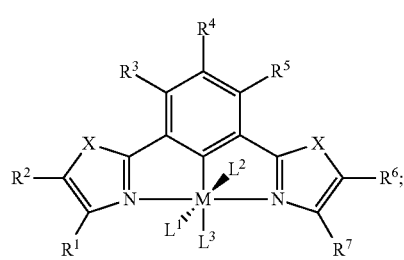

(II)

or

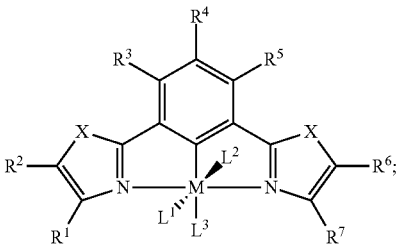

(II)

wherein M is selected from Mo, Tc, Ru, Rh, Pd, Ag, W, Re, Os, Ir, Pt and Au, X is oxygen, $R^1$ to $R^7$ independently of one another are each hydrogen, halogen, R', O—R', or N—R'R", wherein R' is a hydrocarbon group which may optionally contain heteroatoms and R" is H or has a meaning as defined for R', it also being possible for two or more groups $R^1$ to $R^7$ to form fused ring systems, and $L^1$, $L^2$, and $L^3$ independently of one another are each a negatively charged or neutral ligand, it being possible for two or more of the ligands $L^1$, $L^2$, and $L^3$ to be bound to one another.

2. The complex according to claim 1, wherein M in formula (II) is Ir(III), Ru(II), or Os(II), M in formula (II) is Pt(II), Pd(II), Ir(III), Ru(II), or Os(II).

3. The complex according to claim 1, wherein $R^1$ to $R^7$ or R' or R" independently of one another are each hydrogen, alkyl, aryl, heteroaryl, alkenyl, or alkynyl groups which may optionally be substituted.

4. The complex according to claim 1, wherein $R^1$ to $R^7$ or R' or R", independently of one another, are each substituted with one or more substituents selected from the group consisting of halogens and alkyl groups having 1 to 6 C atoms.

5. The complex according to claim 1, wherein $L^1$, $L^2$, and $L^3$ independently of one another are each selected from halogen, pseudohalogen, and ligands which are bound to M via an element from group 16 of the Periodic Table, from group 15 of the Periodic Table, or from group 14 of the Periodic Table.

6. A method for emitting light comprising operating a light emitting device comprising
   (i) an anode,
   (ii) a cathode, and
   (iii) an emitter layer arranged between and in direct or indirect contact with the anode and the cathode, comprising at least one complex according to claim 1.

7. A complex selected from the group consisting of 5,5'-di-tert-butyl-2,2'-m-phenylene-bis-oxazole-2-platinum(II) bromide; 5,5'-diphenyl-2,2'-m-phenylene-bis-oxazole-2-platinum(II) bromide; 2,6-bis(5-ethoxyoxazol-2-yl)phenyl-bromoplatinum(II); 2-(4-methoxycarbonyloxazol-2-yl)-6-(5-ethoxyoxazol-2-yl)phenyl-bromoplatinum(II); (3-oxo-3-ethoxypropynyl)-[2,6-bis(5-ethoxyoxazol-2-yl)phenyl]-platinum(II); (3-hydroxylpropynyl)-[2,6-bis(5-ethoxyoxazol-2-yl)phenyl]-platinum(II); 5,5'-di-tert-butyl-2,2'-in-phenylene-bis-oxazole-2-palladium(II) bromide; 5,5'-diphenyl-2,2'-m-phenylene-bis-oxazole-2-palladium(II) bromide;

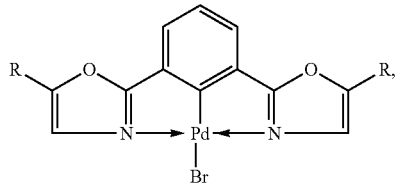
wherein R is selected from Ph;
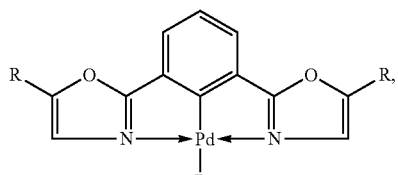
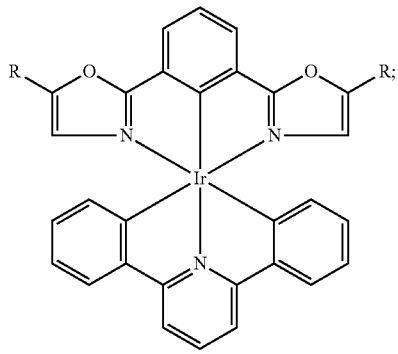
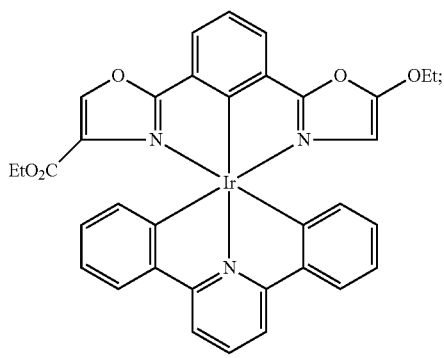
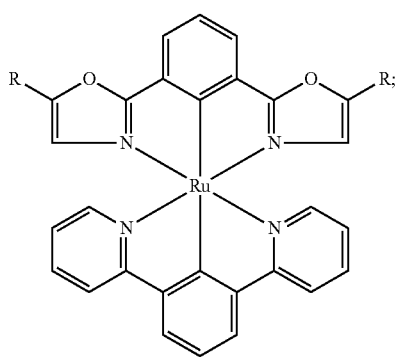
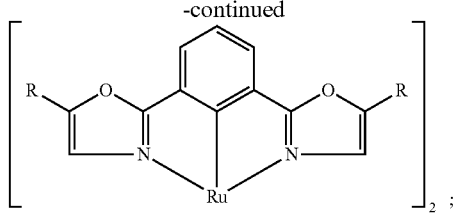
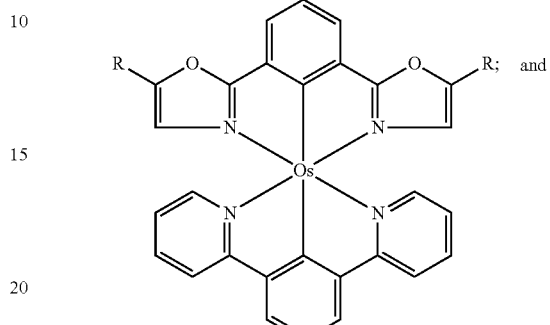
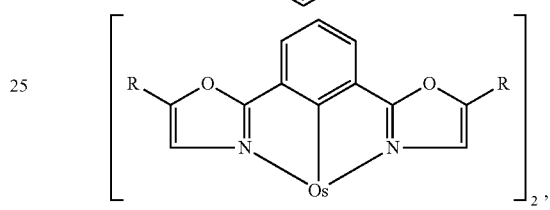
and
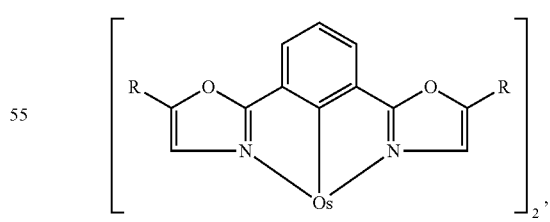
wherein R is selected from t-Bu, OEt, or Ph.
8. A light-emitting device, comprising
(i) an anode,
(ii) a cathode and)
(iii) an emitter layer arranged between and in direct or indirect contact with the anode and the cathode, comprising at least one complex of formula (I) or (II):

(I) 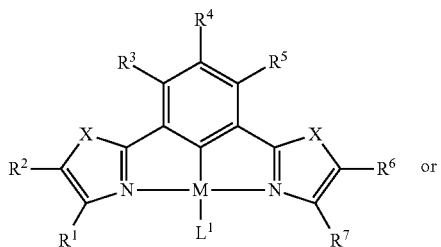

(II) 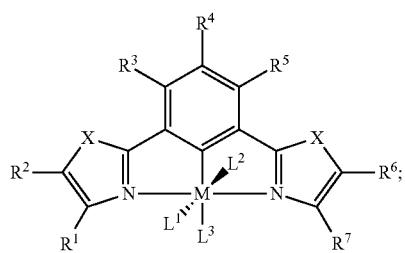

(II) 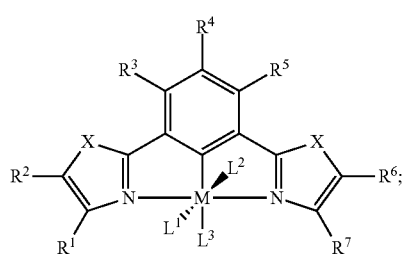

wherein M is selected from Mo, Tc, Ru, Rh, Pd, Ag, W, Re, Os, Ir, Pt and Au, X is oxygen, $R^1$ to $R^7$ independently of one another are each hydrogen, halogen, R', O—R', or N—R'R", wherein R' is a hydrocarbon group which may optionally contain heteroatoms and R" is H or has a meaning as defined for R', it also being possible for two or more groups $R^1$ to $R^7$ to form fused ring systems, and $L^1$, $L^2$, and $L^3$ independently of one another are each a negatively charged or neutral ligand, it being possible for two or more of the ligands $L^1$, $L^2$, and $L^3$ to be bound to one another.

9. The light-emitting device according to claim 8, wherein the light-emitting device further comprises a hole transport layer or/and an electron transport layer.

10. The light-emitting device according to claim 8, wherein the complex contained in the emitter layer is a triplet emitter.

11. The light-emitting device according to claim 8, wherein M is in an oxidation stage 0 to +4.

12. The light-emitting device according to claim 8, wherein the emitter layer contains complexes of formula (I) or/and (II) in a concentration of 1 to 100% by weight, relative to the total weight of the emitter layer.

13. The light-emitting device according to claim 8 wherein the proportion of complexes of formula (I) in the emitter layer is more than 80% by weight relative to the total weight of the emitter layer.

14. The light-emitting device according to claim 13, wherein the complexes of formula (I) in the emitter layer exist as oligomers.

15. The light-emitting device according to claim 8, wherein the proportion of complexes of formula (I) in the emitter layer is more than 10% by weight and up to 80% by weight relative to the total weight of the emitter layer.

16. The light-emitting device according to claim 8, wherein the emitter is selected from 5,5'-di-tert-butyl-2,2'-m-phenylene-bis-oxazole-2-platinum(II) bromide; 5,5'-diphenyl-2,2'-m-phenylene-bis-oxazole-2-platinum(II) bromide; 2,6-bis(5-ethoxyoxazol-2-yl)phenyl-bromoplatinum(II); 2-(4-methoxycarbonyloxazol-2-yl)-6-(5-ethoxyoxazol-2-yl)phenyl-bromoplatinum(II); (3-oxo-3-ethoxypropynyl)-[2,6-bis(5-ethoxyoxazol-2-yl)phenyl]platinum(II); (3-hydroxylpropynyl)-[2,6-bis(5-ethoxyoxazol-2-yl)phenyl]-platinum(II); 5,5'-di-tert-butyl-2,2'-m-phenylene-bis-oxazole-2-palladium(II) bromide; 5,5'-diphenyl-2,2'-m-phenylene-bis-oxazole-2-palladium(II)bromide; or

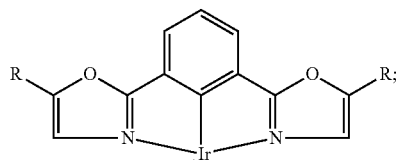

wherein R is selected from Ph or OEt;

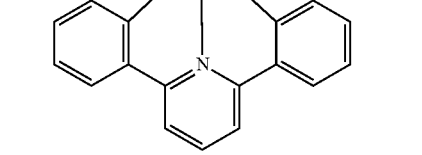

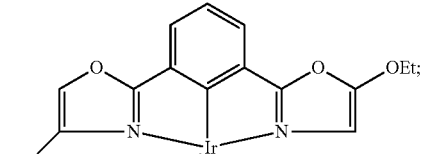

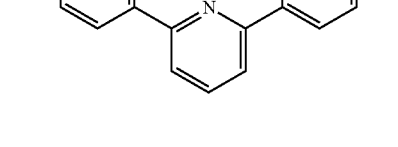

-continued

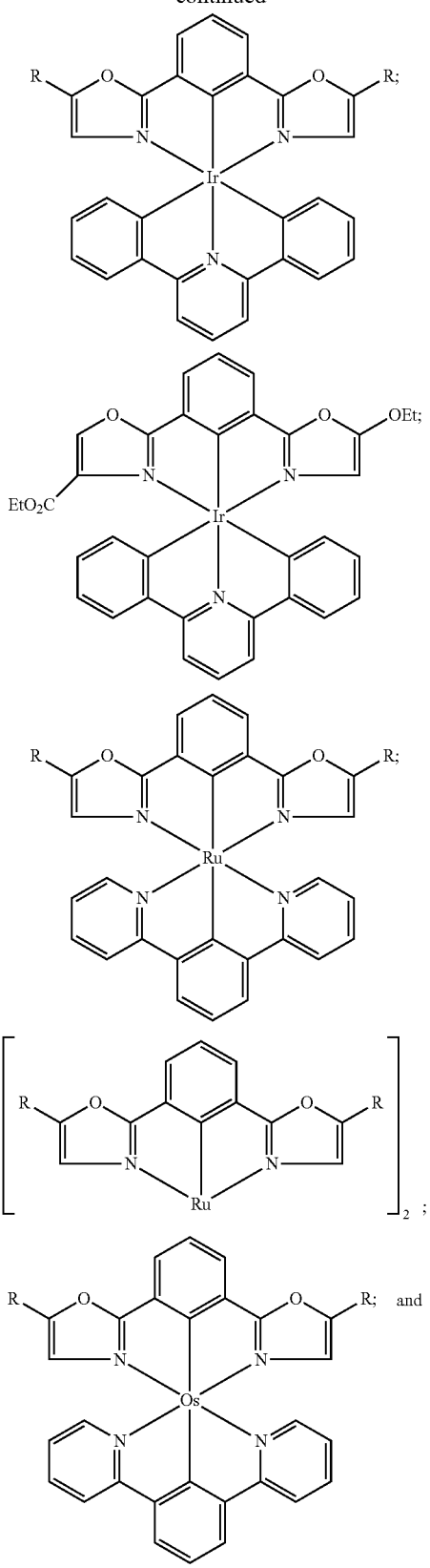

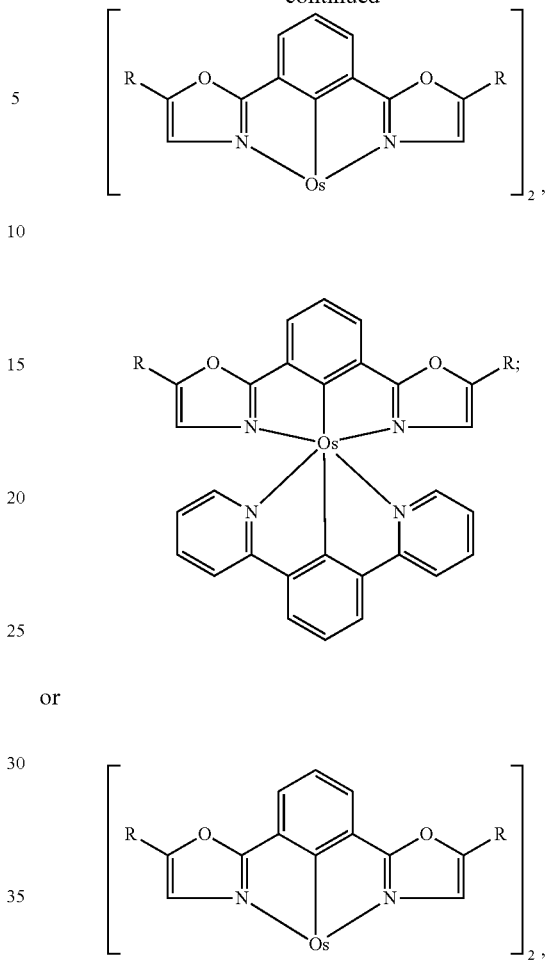

wherein R is selected from t-Bu, OEt, and Ph.

17. The light-emitting device according to claim 8, wherein the light-emitting device comprises at least two different complexes of formula (I) or (II).

18. The light-emitting device according to claim 8, wherein the emitter layer contains complexes of formula (I) wherein M=Pd(II) is in a proportion of more than 80% by weight and complexes of formula (I) wherein M=Pt(II) is in a proportion of less than 10% by weight, in each case relative to the total weight of the emitter layer.

19. The light-emitting device according to claim 8, wherein the light-emitting device further comprises crystalline or/and quasi-crystalline layers of complexes of formula (I).

20. The light-emitting device according to claim 8, wherein the light-emitting device is an OLED.

21. The light-emitting device according to claim 8, wherein the light-emitting device is a display or/and a lighting device.

22. A method for producing a light-emitting device according to claim 8, wherein at least one complex of formula (I) or (II) is incorporated in the emitter layer by means of vacuum sublimation.

23. A method for producing a light-emitting device according to claim 8, wherein at least one complex of formula (I) or (II) is incorporated in the emitter layer via a wet chemical process.

* * * * *